United States Patent
Moszner et al.

(10) Patent No.: US 11,401,287 B2
(45) Date of Patent: Aug. 2, 2022

(54) LONG-WAVE ABSORBING PHOTOINITIATORS

(71) Applicant: IVOCLAR VIVADENT AG, Schaan (LI)

(72) Inventors: Norbert Moszner, Triesen (LI); Yohann Catel, Sevelen (CH); Pascal Fässler, Wangs (CH); Michael Haas, Graz (AT); Judith Radebner, Göriach (AT); Harald Stüger, Graz (AT)

(73) Assignee: Ivoclar Vivadent AG, Schaan (LI)

(*) Notice: Subject to any disclaimer, the term of this patent is extended or adjusted under 35 U.S.C. 154(b) by 0 days.

(21) Appl. No.: 17/178,678

(22) Filed: Feb. 18, 2021

(65) Prior Publication Data

US 2021/0261578 A1 Aug. 26, 2021

(30) Foreign Application Priority Data

Feb. 21, 2020 (EP) .................................. 20020082

(51) Int. Cl.

| | |
|---|---|
| *C08F 2/46* | (2006.01) |
| *C08F 2/50* | (2006.01) |
| *C08G 61/04* | (2006.01) |
| *C07F 7/30* | (2006.01) |
| *A61K 6/62* | (2020.01) |
| *C08F 220/18* | (2006.01) |

(52) U.S. Cl.
CPC .................. *C07F 7/30* (2013.01); *A61K 6/62* (2020.01); *C08F 2/50* (2013.01); *C08F 220/18* (2013.01)

(58) Field of Classification Search
CPC .. C08F 2/50; C08F 4/70; C08F 220/18; C08L 33/04; C08L 33/26; C07F 7/2208; C07F 7/30; A61K 6/62; A61K 6/30; A61K 6/887
USPC .................. 522/66, 6, 189, 184, 71, 1; 520/1
See application file for complete search history.

(56) References Cited

U.S. PATENT DOCUMENTS

| | | | |
|---|---|---|---|
| 4,071,424 A | 1/1978 | Dart et al. | |
| 4,457,818 A | 7/1984 | Denyer et al. | |
| 4,525,256 A | 6/1985 | Martin | |
| 6,043,361 A | 3/2000 | Evans et al. | |
| 6,344,556 B1 | 2/2002 | Evans et al. | |
| 6,479,592 B2 | 11/2002 | Rheinberger et al. | |
| 7,585,901 B2 | 9/2009 | Moszner et al. | |
| 7,605,190 B2 | 10/2009 | Moszner et al. | |
| 8,829,067 B2 * | 9/2014 | Moszner ................... | C08F 4/72 522/66 |
| 10,787,468 B2 | 9/2020 | Moszner et al. | |

FOREIGN PATENT DOCUMENTS

DE 19903177 A1 7/2000

OTHER PUBLICATIONS

Fruhwirt et al, The chemistry of acylgermanes: Triacylgermenolates Represent Valuable Building Blocks for the Synthesis of a Varity of Germanium-Based Photoinitiators, Sep. 29, 2020, Inorg. Chem. 59, 15204-15217 (Year: 2020).*
Fouassier, J.P., Rabek, J.F., "Radiation Curing in Polymer Science and Technology—Photoinitiating Systems" vol. II, pp. 210-225 and pp. 456-461, Elsevier Applied Science, Elsevier Science Publishers LTD, London and New York, 1993.

* cited by examiner

*Primary Examiner* — Jessica Whiteley
(74) *Attorney, Agent, or Firm* — Ann M. Knab; Thad McMurray

(57) ABSTRACT

Compounds according to general formula (I)

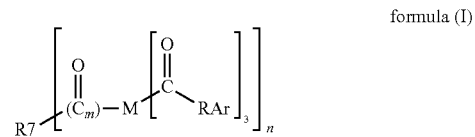

in which M is Ge or Sn, RAr is

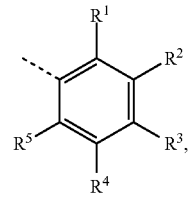

$R^1$, $R^2$, $R^3$, $R^4$, $R^5$, independently of one another in each case, are —H, —F, —Cl, —$OR^6$, —$SR^6$, —$N(R^6)_2$, —$CF_3$, —CN, —$NO_2$, —$COOR^6$, —$CONHR^6$, a branched, cyclic or preferably linear $C_{1-20}$ alkyl, $C_{2-20}$ alkenyl, $C_{1-20}$ alkyloxy or a $C_{2-20}$ alkenoxy radical, which can be interrupted one or more times by O, S or —$NR^6$— and substituted by one or more polymerizable groups and/or radicals $R^6$, $R^6$ is H, a branched, cyclic or preferably linear $C_{1-20}$ alkyl or $C_{2-20}$ alkenyl radical, $R^7$ is a chemical bond, an n-valent aromatic radical or a branched, cyclic or preferably linear $C_{1-20}$ alkylene radical, which can be interrupted one or more times by O, S or —$NR^6$— and substituted by one or more polymerizable groups, =O and/or radicals $R^6$, n is 2 or 3 and m is 0 or 1. The compounds are particularly suitable as photoinitiators for radical polymerization and in particular for the production of dental materials.

18 Claims, No Drawings

LONG-WAVE ABSORBING PHOTOINITIATORS

CROSS-REFERENCE TO RELATED APPLICATIONS

This application claims priority to European patent application No. 20020082.2 filed on Feb. 21, 2020, the disclosure of which is incorporated herein by reference in its entirety.

FIELD OF THE INVENTION

The present invention relates to acyl germanium and acyl tin compounds which are suitable as photoinitiators for curing radically polymerizable materials. The initiators are characterized in that they can be activated with visible light. They can be used for the production of adhesives, coatings, cements, composites, shaped parts, such as rods, plates, discs or lenses, and in particular for the production of dental materials.

BACKGROUND

The photoinitiator used plays a decisive role in the curing of photopolyreactive resins. When irradiated with UV or visible light, the photoinitiator absorbs the light and forms the polyreaction-initiating species. In the event of radical photopolymerization these are free radicals.

The photoinitiators are divided into two classes based on the chemical mechanism of radical formation. When irradiated, Norrish type I photoinitiators form free radicals by unimolecular bond cleavage. When irradiated, Norrish type II photoinitiators undergo a bimolecular reaction, wherein in the excited state the photoinitiator reacts with a second molecule, the so-called coinitiator, and forms the polymerization-initiating radicals by electron and proton transfer. Type I and type II photoinitiators are used for UV light curing; to date almost exclusively type II photoinitiators, with the exception of bisacyl dialkyl germanium compounds, have been used for the visible range.

Above all, transparent coatings with small layer thickness can be UV-cured due to the small wavelength of the UV light. The limits of UV curing are reached in the case of strong coloration or pigmentation and in the case of greater layer thicknesses. In these cases, complete curing is not possible with UV light. If larger depths of cure are required, such as for example in the curing of light-curing dental filling composites, visible light is usually used for the irradiation. The photoinitiator system most frequently used for this is the combination of an α-diketone with an amine coinitiator, which is described e.g. in GB 1 408 265.

U.S. Pat. Nos. 4,457,818 and 4,525,256, which are hereby incorporated by reference in their entirety, disclose dental materials which contain an α-diketone such as camphorquinone as photoinitiator. Camphorquinone has an absorption maximum at a wavelength of 468 nm, and therefore has a strong yellow colouring, with the result that materials initiated with camphorquinone/amine often have a clear yellowness after curing. This is particularly disadvantageous in the case of materials with bright white shades.

EP 1 905 415 A1 and corresponding U.S. Pat. No. 7,605,190, which is hereby incorporated by reference in its entirety, discloses radically polymerizable dental materials which contain bisacyl dialkyl germanium compounds as Norrish type I photoinitiators. The initiators can be activated with blue light, which is often used for curing in the dental field, and do not result in discolorations of the materials. The specifically disclosed compounds have absorption maxima in the range of from 411.5 nm to 418.5 nm.

EP 2 103 297 A1 and corresponding U.S. Pat. No. 8,829,067, which is hereby incorporated by reference in its entirety, discloses radically polymerizable dental materials which contain acyl germanium compounds with several germanium atoms as photoinitiators. These initiators are characterized by a low cytotoxicity and a high activity, and make a high depth of cure possible without disruptive discolorations of the materials. The specifically disclosed 1,6-bis[4-(trimethylgermylcarbonyl)phenoxy]hexane has an absorption maximum of 400.5 nm.

Tetrafunctional acyl germanes and stannanes which are suitable as photoinitiators for dental purposes are known from EP 3 150 641 A1 and corresponding U.S. Pat. No. 10,533,025, which is hereby incorporated by reference in its entirety. When irradiated with visible light these yield high depths of cure and can be produced more easily than bisacyl germanes. A disadvantage is that these initiators are comparatively expensive. The specifically disclosed compounds have absorption maxima in the range of from 288 nm to 419 nm.

SUMMARY

The object of the invention is to provide photoinitiators for radical polymerization by visible light which do not have the disadvantages of known initiators, which are characterized by an improved curing characteristic and which are easy to produce compared with the state of the art. In addition, the initiators should, in particular, enable large depths of curing.

DETAILED DESCRIPTION

This object is achieved according to the invention by multifunctional aromatic acyl germanium and acyl tin compounds according to general formula (I),

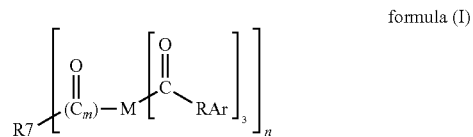

formula (I)

in which the variables have the following meanings:
M Ge or Sn,
RAr

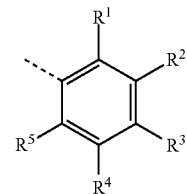

$R^1$, $R^2$, $R^3$, $R^4$, $R^5$ independently of one another in each case —H, —F, —Cl, —$OR^6$, —$SR^6$, —$N(R^6)_2$, —$CF_3$, —CN, —$NO_2$, —$COOR^6$, —$CONHR^6$, a branched, cyclic or preferably linear $C_{1-20}$ alkyl, $C_{2-20}$ alkenyl, $C_{1-20}$ alkyloxy or a $C_{2-20}$ alkenoxy radical, which can be interrupted one or more times by O, S or —NR⁶— and which can be substituted by one or more polymerizable groups and/or radicals R⁶, R⁶ in each case independently of one another H, a branched, cyclic or preferably linear $C_{1-20}$ alkyl or $C_{2-20}$ alkenyl radical, R⁷ a chemical bond, an n-valent aromatic radical or an n-valent branched, cyclic or preferably linear $C_{1-20}$ alkylene radical, which can be interrupted one or more times by O, S or —NR⁶— and which can be substituted by one or more polymerizable groups, =O and/or radicals R⁶, n 2 or 3, m 0 or 1.

The group R⁷ is substituted n times by the group in brackets or, if R⁷ is a chemical bond, connects two of the groups in brackets.

R⁷ is preferably an n-valent aromatic radical or an n-valent branched, cyclic or preferably linear $C_{2-20}$ alkylene radical, more preferably a $C_{3-20}$ alkylene radical, which can be interrupted one or more times by O, S or —NR⁶— and which can be substituted by one or more polymerizable groups, =O and/or radicals R⁶.

Formula (I) and the remaining formulae shown herein cover all stereoisomeric forms as well as mixtures of different stereoisomeric forms, such as e.g. racemates. Formula (I) extends only to those compounds which are compatible with the theory of chemical valence. The indication that a radical is interrupted e.g. by one or more O atoms or groups is to be understood to mean that these atoms or groups are inserted in each case into the carbon chain of the radical. These atoms or groups are thus bordered on both sides by C atoms and cannot be terminal. $C_1$ radicals cannot be interrupted, branched or cyclic. By aromatic hydrocarbon radicals is meant, in accordance with the usual nomenclature, also those radicals which contain aromatic and non-aromatic groups. If R⁷ is a chemical bond, n can only be 2.

In the case of hydrocarbon radicals which contain carbon atoms and heteroatoms, the number of heteroatoms is always less than the number of carbon atoms irrespective of substituents.

In all cases the above-named groups are preferably interrupted by 0 to 3, particularly preferably 0 to 2 atoms or groups and are quite particularly preferably not interrupted.

Even if not explicitly indicated, alkyl and alkylene stand for linear and branched groups, wherein linear alkyl radicals are preferred in all cases.

By aromatic radicals is preferably meant radicals with 6 to 18, particularly preferably 6 to 14 and quite particularly preferably radicals with 6 carbon atoms, in particular a p-phenylene group (n=2) or benzene-1,3,5-triyl group (n=3).

Preferred polymerizable groups which can be present as substituents in the above radicals are vinyl, (meth)acryl and (meth)acrylamide, particularly preferably (meth)acryl, and quite particularly preferably methacryl ($H_2C=C(-CH_3)-CO-$), groups. The radicals R¹ to R⁵ and R⁷ are preferably substituted with 0 to 3, more preferably 0 to 1 polymerizable groups and are quite particularly preferably unsubstituted. The polymerizable groups are preferably arranged terminal.

The variables of formula (I) preferably have the following meanings:

M Ge or Sn,

RAr

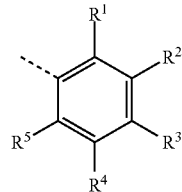

R¹, R², R³, R⁴, R⁵ independently of one another in each case —H, —F, —Cl, —OR⁶, —CF₃, —CN, —COOR⁶, —CONHR⁶, a branched, cyclic or preferably linear $C_{1-20}$ alkyl, $C_{2-20}$ alkenyl, $C_{1-20}$ alkyloxy or a $C_{2-20}$ alkenoxy radical, which can be interrupted one or more times by O or S and which can be substituted by one or more polymerizable groups and/or radicals R⁶, R⁶H, an aromatic radical or a branched, cyclic or preferably linear $C_{1-10}$ alkyl radical, $C_{2-10}$ alkenyl radical, R⁷ an n-valent benzene radical, a branched or linear n-valent $C_{2-10}$ alkylene radical, preferably a $C_{3-10}$ alkylene radical, which can be interrupted one or more times by O or S and substituted by one or more polymerizable groups, =O and/or radicals R⁶, n 2, m 0 or 1.

The variables of formula (I) particularly preferably have the following meanings:

M Ge or Sn,

RAr

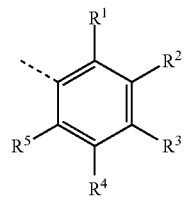

R¹, R², R³, R⁴, R⁵ independently of one another in each case —H or a $C_{1-3}$ alkyl radical, preferably methyl, R⁷ an n-valent benzene radical or an n-valent, linear $C_{2-3}$ alkyl radical, preferably a $C_{2-6}$ alkyl radical, more preferably a $C_{3-6}$ alkyl radical, n 2, m 0 or 1.

Those compounds in which R² and R⁴ are in each case H and R¹, R³ and R⁵ are in each case H or methyl and most preferably are methyl are quite particularly preferred. In this case RAr is:

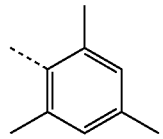

The preferred, particularly preferred and quite particularly preferred definitions indicated for the individual variables can be selected in each case independently of one another. Compounds in which all variables have the preferred, particularly preferred and quite particularly preferred definitions are naturally particularly suitable according to the invention.

According to an embodiment of the invention those compounds of formula (I) in which m=1 are preferred. These compounds can be represented by formula (II):

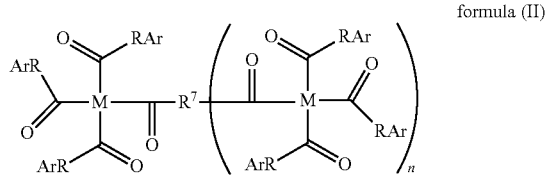
formula (II)

Preferred compounds of formula (II) are those compounds in which the variables of formula (II) have the following meanings:
M Ge or Sn
RAr

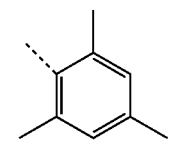

R$^7$

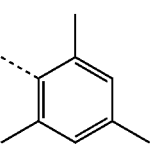

n 2.

According to a further embodiment of the invention the variables of formula (II) preferably have the following meanings:
M Ge
RAr

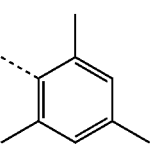

R$^7$

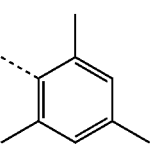

n 3.

According to a further embodiment of the invention those compounds of formula (I) in which m=0 are preferred. These compounds can be represented by formula (III):

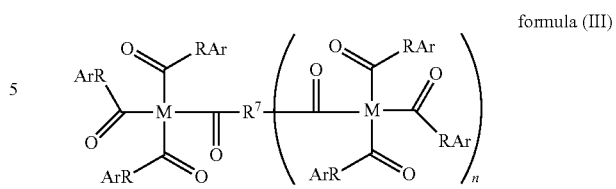
formula (III)

Preferred compounds of formula (III) are those compounds in which the variables of formula (III) have the following meanings:
M Ge
RAr

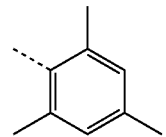

R$^7$ C$_2$-C$_8$ alkylene, particularly preferably —C$_4$H$_8$—
n 2.

The aromatic acyl germanium or acyl tin compounds according to the invention of general formula (I) are not known from the state of the art. The synthesis of the compounds is preferably effected starting from the corresponding aromatic trisacyl metal enolates (TrAME): where M=Ge starting from the trisacyl germanium enolates (TrAGeE) and with M=Sn starting from the trisacyl tin enolates (TrASnE), which can be obtained by reaction of the corresponding tetraacyl metal compound, i.e. of a corresponding tetraacyl germane (TAGe, M=Ge) or tetraacyl stannane (TASn, M=Sn), with potassium tert.-butylate (KOtBu):

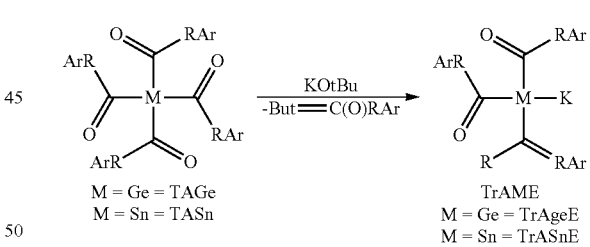

M = Ge = TAGe
M = Sn = TASn

TrAME
M = Ge = TrAgeE
M = Sn = TrASnE

Moreover, the synthesis of the trisacyl metal enolate (TrAME) can be effected in a one-pot reaction, such that tetrakis(trimethylsilyl) germane or stannane is first reacted with KOtBu to form the corresponding tris(trimethylsilyl) germanide or stannide, which is then further reacted with 3 equivalents of an aromatic acid fluoride to form the trisacyl metal enolate (TrAME):

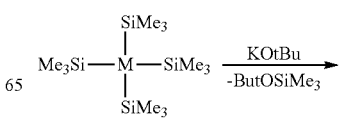

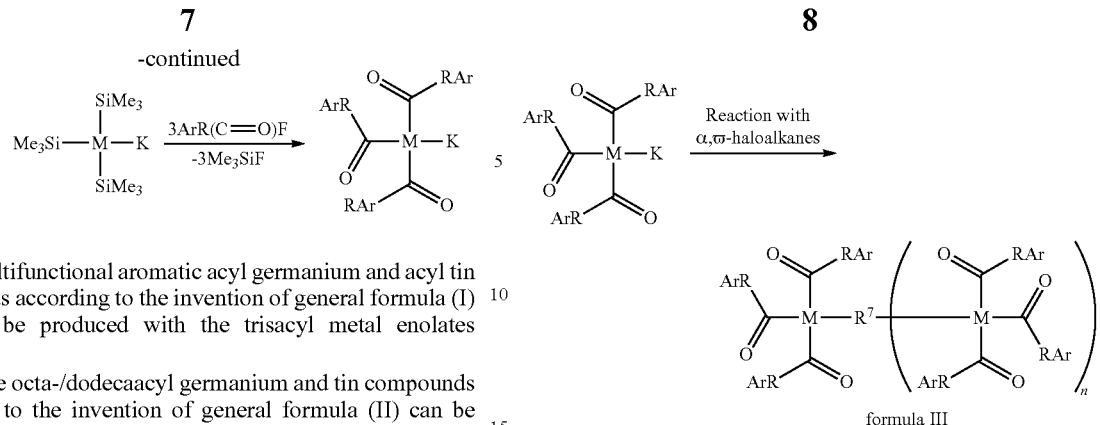

The multifunctional aromatic acyl germanium and acyl tin compounds according to the invention of general formula (I) can then be produced with the trisacyl metal enolates (TrAME).

Thus the octa-/dodecaacyl germanium and tin compounds according to the invention of general formula (II) can be obtained by reaction of the trisacyl metal enolate with di- or triacid chlorides:

Specific example of a hexaacyl digermanium derivative:

Specific Example of Octaacyl Germanium Derivatives:

The hexaacyl/nonaacyl germanium and tin compounds according to the invention of general formula (III) can be produced by reaction of the trisacyl metal enolates with α,ω-di- or trihaloalkanes:

Specific examples of particularly preferred compounds of formula (I) are:

-continued
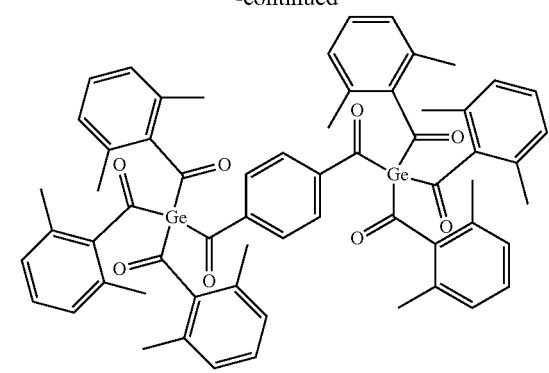
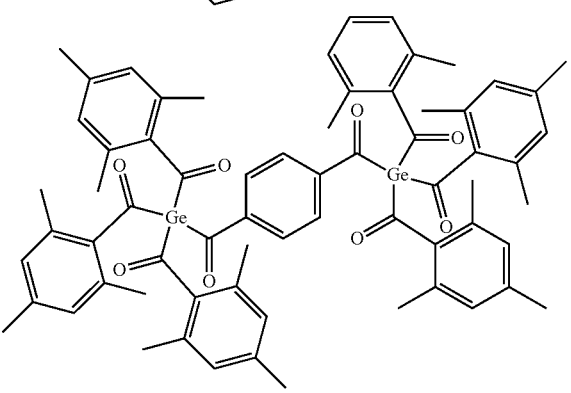
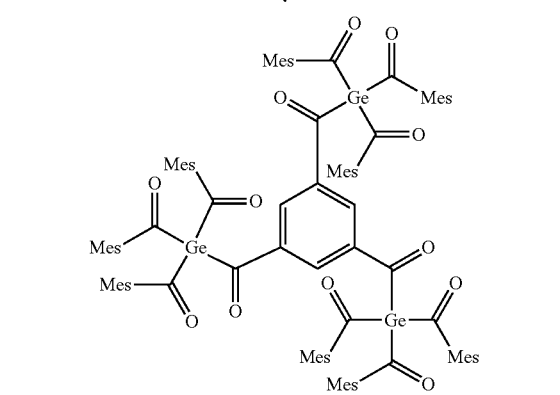
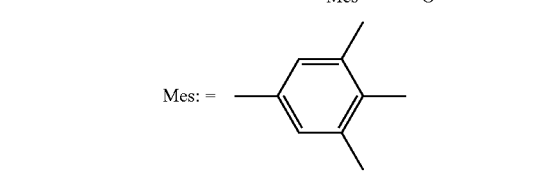
Mes: = 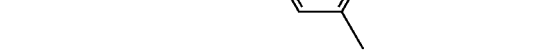
-continued
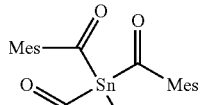
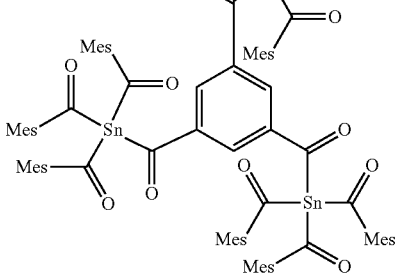
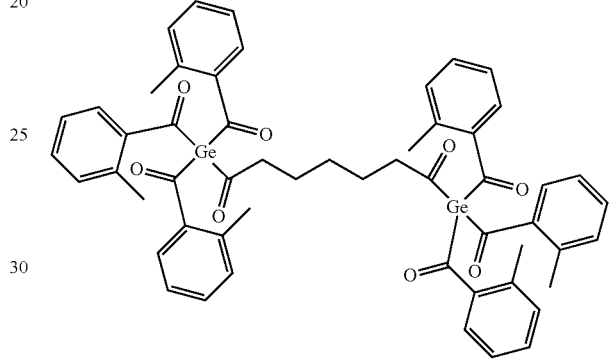
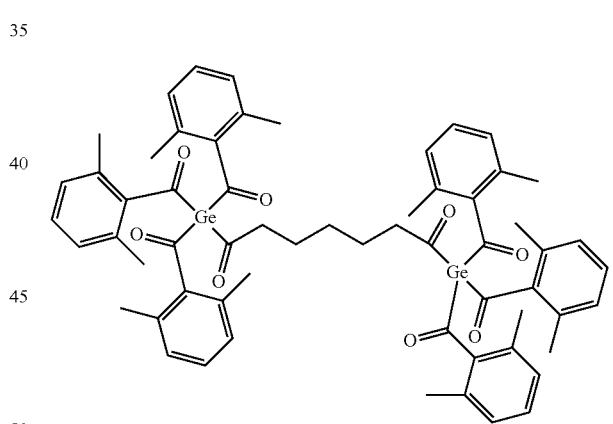
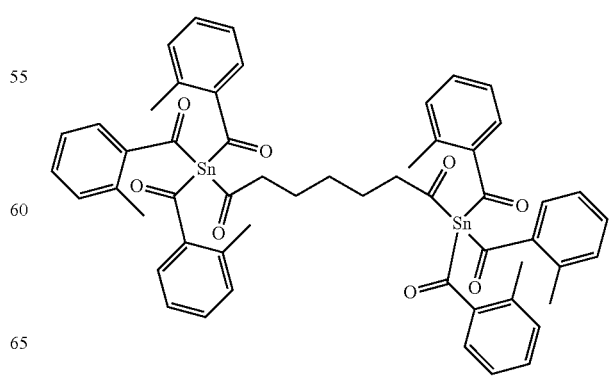

-continued

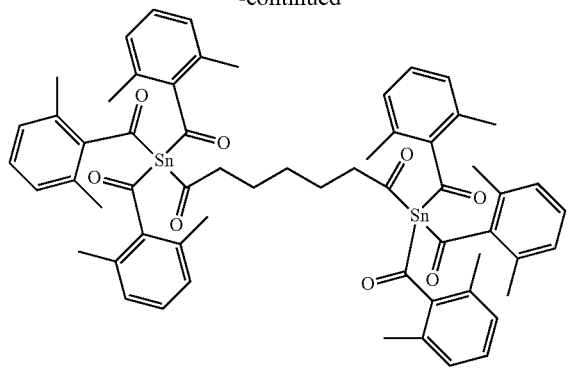

The compounds according to the invention of general formula (I) surprisingly have an absorption range for visible light which is clearly shifted towards larger wavelengths compared with structurally similar known photoinitiators. They thus allow the polymerization to be initiated with longer-wave light and make larger depths of cure possible. Moreover, the compounds of formula (I) are characterized by very high extinction coefficients of the absorption in the visible range. In low concentration they are therefore already effective as photoinitiators for polyreactions initiated by visible light. The photoinitiators of formula (I) in addition have a very good bleaching behaviour, i.e. they are very quickly and practically completely decoloured during the polymerization. Additionally, they are easy to obtain synthetically.

The compounds according to the invention of general formula (I) are particularly suitable as photoinitiators for polyreactions, in particular as initiators for polyaddition and for the thiol-ene reaction and quite particularly for radical polymerization. For this, they are preferably combined with at least one polymerizable binder. Binders based on monomers which can be polymerized by polyaddition are preferred, binders based on radically polymerizable monomers are particularly preferred. Compositions which contain at least one compound of formula (I) and at least one monomer are likewise a subject of this invention.

Mono- or multifunctional (meth)acrylates or a mixture thereof are particularly suitable as radically polymerizable monomers. By monofunctional (meth)acrylates is meant compounds with one, by multifunctional (meth)acrylates is meant compounds with two or more, preferably 2 to 3, polymerizable groups.

Preferred examples are methyl, ethyl, hydroxyethyl, butyl, benzyl, tetrahydrofurfuryl or isobornyl (meth)acrylate, bisphenol A di(meth)acrylate, bis-GMA (an addition product of methacrylic acid and bisphenol A diglycidyl ether), UDMA (an addition product of 2-hydroxyethyl methacrylate and 2,2,4-trimethylhexamethylene diisocyanate), di-, tri- or tetraethylene glycol di(meth)acrylate, trimethylolpropane tri(meth)acrylate, pentaerythritol tetra(meth)acrylate, 1,4-butanediol di(meth)acrylate, 1,10-decanediol dimethacrylate ($D_3MA$), bis(methacryloyloxymethyl)tricyclo-[5.2.1.0$^{2,6}$]decane (DCP), as well as glycerol di- and glycerol tri(meth)acrylate, 1,4-butanediol di(meth)acrylate, 1,10-decanediol diacrylate, 1,12-dodecanediol di(meth) acrylate and mixtures thereof.

Compositions which contain at least one radically polymerizable monomer with 2 or more, preferably 2 to 3, radically polymerizable groups are particularly preferred. Polyfunctional monomers have crosslinking properties.

Hydrolysis-stable monomers, such as hydrolysis-stable mono(meth)acrylates, e.g. mesityl methacrylate or 2-(alkoxymethyl)acrylic acids, e.g. 2-(ethoxymethyl)acrylic acid, 2-(hydroxymethyl)acrylic acid, N-mono- or -disubstituted acrylamides, such as e.g. N-ethylacrylamide, N,N-dimethacrylamide, N-(2-hydroxyethyl)acrylamide or N-methyl-N-(2-hydroxyethyl)acrylamide, N-monosubstituted methacrylamides, such as e.g. N-ethylmethacrylamide or N-(2-hydroxyethyl)methacrylamide as well as N-vinylpyrrolidone or allyl ether can advantageously also be used as radically polymerizable monomers.

Preferred examples of hydrolysis-stable crosslinking monomers are urethanes of 2-(hydroxymethyl)acrylic acid and diisocyanates, such as 2,2,4-trimethylhexamethylene diisocyanate or isophorone diisocyanate, crosslinking pyrrolidones, such as e.g. 1,6-bis(3-vinyl-2-pyrrolidonyl)-hexane, or commercially available bisacrylamides such as methylene or ethylene bisacrylamide, bis(meth)acrylamides, such as e.g. N,N'-diethyl-1,3-bis(acrylamido)-propane, 1,3-bis(methacrylamido)-propane, 1,4-bis(acrylamido)-butane or 1,4-bis(acryloyl)-piperazine, which can be synthesized by reaction of the corresponding diamines with (meth)acrylic acid chloride. Monomers that are liquid at room temperature, which can be used as diluting monomers, are preferred.

Low-shrinkage radically ring-opening polymerizable monomers such as e.g. mono- or multifunctional vinylcyclopropanes or bicyclic cyclopropane derivatives, preferably those described in DE 196 16 183 C2 or EP 1 413 569 A1, or cyclic allyl sulfides, preferably those described in U.S. Pat. Nos. 6,043,361 and 6,344,556, can furthermore also be used as radically polymerizable binders. These can advantageously also be used in combination with the di(meth)acrylate crosslinkers listed above. Preferred ring-opening polymerizable monomers are vinylcyclopropanes, such as 1,1-di(ethoxycarbonyl)- or 1,1-di(methoxycarbonyl)-2-vinylcyclopropane or the esters of 1-ethoxycarbonyl- or 1-methoxycarbonyl-2-vinylcyclopropanecarboxylic acid with ethylene glycol, 1,1,1-trimethylolpropane, 1,4-cyclohexanediol or resorcinol. Preferred bicyclic cyclopropane derivatives are 2-(bicyclo[3.1.0]hex-1-yl)acrylic acid methyl or ethyl esters and their disubstitution products in the 3 position, such as (3,3-bis(ethoxycarbonyl)bicyclo[3.1.0] hex-1-yl)acrylic acid methyl or ethyl esters. Preferred cyclic allyl sulfides are the addition products of 2-(hydroxymethyl)-6-methylene-1,4-dithiepane or 7-hydroxy-3-methylene-1,5-dithiacyclooctane with 2,2,4-trimethylhexamethylene-1,6-diisocyanate or the asymmetrical hexamethylene diisocyanate trimer (Desmodur® VP LS 2294 from Bayer AG).

Further preferred radically polymerizable monomers are vinyl esters, vinyl carbonates and vinyl carbamates. Moreover, styrene, styrene derivatives, divinylbenzene, unsaturated polyester resins as well as allyl compounds or radically polymerizable polysiloxanes, which can be produced from suitable methacrylsilanes, such as e.g. 3-(methacryloyloxy)propyltrimethoxysilane, and are described e.g. in DE 199 03 177 C2, can also be used as radically polymerizable monomers. By styrene derivatives is meant compounds in which the phenyl group of the styrene, but not the vinyl group, is mono- or polysubstituted by simple groups, such as $C_1$-$C_{10}$ alkyl, Cl, Br, OH, $CH_3O$, CHO, $C_2H_5O$, COOH or carboxylic acid ester groups.

Moreover, mixtures of the above-named monomers with radically polymerizable, acid-group-containing monomers, which are also called adhesive monomers, can also be used as radically polymerizable binders. Preferred acid-group-containing monomers are polymerizable carboxylic acids, such as maleic acid, acrylic acid, methacrylic acid, 2-(hydroxymethyl)acrylic acid, 4-(meth)acryloyloxyethyltrimellitic acid anhydride, 10-methacryloyloxydecylmalonic acid, N-(2-hydroxy-3-methacryloyloxypropyl)-N-phenylglycine or 4-vinylbenzoic acid.

Radically polymerizable phosphonic acid monomers, in particular vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid or 2-[2-dihydroxyphosphoryl)-ethoxymethyl]-acrylic acid ethyl or 2,4,6-trimethylphenyl ester are particularly suitable as adhesive monomers.

In addition, acidic polymerizable phosphoric acid esters, in particular 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritol-pentamethacryloyloxy phosphate, 10-methacryloyloxydecyl dihydrogen phosphate, dipentaerythritol-pentamethacryloyloxy phosphate, phosphoric acid mono-(1-acryloyl-piperidin-4-yl) ester, 6-(methacrylamido)hexyl dihydrogen phosphate and 1,3-bis-(N-acryloyl-N-propyl-amino)-propan-2-yl dihydrogen phosphate, are suitable as adhesive monomers.

Furthermore, polymerizable sulfonic acids are also suitable as adhesive monomers, in particular vinylsulfonic acid, 4-vinylphenylsulfonic acid or 3-(methacrylamido)propylsulfonic acid.

Thiol-ene resins which contain mixtures of mono- or multifunctional mercapto compounds and di- or multifunctional unsaturated monomers, above all allyl or norbornene compounds, are particularly suitable as binders curable by polyaddition.

Examples of mono- or multifunctional mercapto compounds are o-, m- or p-dimercaptobenzene and esters of thioglycolic or of 3-mercaptopropionic acid of ethylene, propylene or butylene glycol, hexanediol, glycerol, trimethylolpropane or pentaerythritol.

Examples of di- or multifunctional allyl compounds are esters of allyl alcohol with di- or tricarboxylic acids, such as malonic, maleic, glutaric, succinic, adipic, sebacic, phthalic, terephthalic or gallic acid, as well as mono- or trifunctional allyl ethers, such as e.g. diallyl ether, α,ω-bis[allyloxy] alkanes, resorcinol or hydroquinone diallyl ether as well as pyrogallol triallyl ether, or other compounds such as e.g. 1,3,5-triallyl-1,3,5-triazine-2,4,6-(1H,3H,5H)-trione, tetraallylsilane or tetraallyl orthosilicate.

Examples of di- or multifunctional norbornene compounds are Diels-Alder addition products of cyclopentadiene or furan with di- or multifunctional (meth)acrylates, as well as esters and urethanes of 5-norbornene-2-methanol or 5-norbornen-2-ol with di- or polycarboxylic acids, such as e.g. malonic, maleic, glutaric, succinic, adipic, sebacic, phthalic, terephthalic or gallic acid, with di- or polyisocyanates, such as hexamethylene diisocyanate or its cyclic trimer, 2,2,4-trimethylhexamethylene diisocyanate, toluylene diisocyanate or isophorone diisocyanate.

In addition to acyl germanium compounds of general formula (I), the compositions according to the invention can advantageously additionally also contain one or more known photoinitiators (cf. J. P. Fouassier, J. F. Rabek (Ed.), Radiation Curing in Polymer Science and Technology, Vol. II, Elsevier Applied Science, London and New York 1993) for the UV or visible range. In particular, combinations with Norrish type I photoinitiators, above all acyl or bisacyl phosphine oxides, such as for example the commercially available compounds 2,4,6-trimethylbenzoyldiphenylphosphine oxide and bis(2,4,6-trimethylbenzoyl)phenylphosphine oxide, are suitable. Monoacyltrialkyl, diacyldialkyl germanium, triacylalkyl and tetraacyl germanium compounds, such as e.g. benzoyltrimethyl germanium, dibenzoyldiethyl germanium or bis(4-methoxybenzoyl)diethyl germanium as well as tetrabenzoyl germanium, are particularly suitable. Further preferred mixtures are initiator combinations which contain compounds of general formula (I) in combination with aromatic diaryl iodonium or triaryl sulfonium salts, for example the commercially available compounds 4-octyloxyphenyl-phenyl-iodonium hexafluoroantimonate or isopropylphenyl-methylphenyl-iodonium tetrakis (pentafluorophenyl)borate.

Moreover, in addition to the compounds of general formula (I) for dual curing the compositions according to the invention can also contain azo compounds, such as 2,2'-azobis(isobutyronitrile) (AIBN) or azobis-(4-cyanovaleric acid), or peroxides, such as dibenzoyl peroxide, dilauroyl peroxide, tert-butyl peroctoate, tert-butyl perbenzoate or di-(tert-butyl) peroxide. To accelerate the initiation by means of peroxides, combinations with aromatic amines can also be used. Preferred redox systems are combinations of benzoyl peroxide with amines, such as N,N-dimethyl-p-toluidine, N,N-dihydroxyethyl-p-toluidine, p-dimethylaminobenzoic acid ethyl ester or structurally related systems. In addition, redox systems consisting of peroxides and reducing agents, such as e.g. ascorbic acid, barbiturates or sulfinic acids, or combinations of hydroperoxides with reducing agents and catalytic metal ions, such as e.g. a mixture of cumene hydroperoxide, a thiourea derivative and copper(II) acetylacetonate, are also suitable for dual curing.

The compositions according to the invention can advantageously moreover contain one or more organic or preferably inorganic fillers. Fibrous and in particular particulate fillers are preferred.

Nanofibres, glass fibres, polyamide fibres and carbon fibres are preferred as fibrous fillers. By nanofibres is meant fibres with a length of less than 100 nm. Fibrous fillers are particularly suitable for the production of composite materials.

Preferred inorganic fillers are amorphous spherical nanoparticulate fillers based on oxides, such as pyrogenic silica or precipitated silica, $ZrO_2$ and $TiO_2$ or mixed oxides of $SiO_2$, $ZrO_2$ and/or $TiO_2$, microfine fillers, such as quartz, glass ceramic or glass powder, and radiopaque fillers, such as ytterbium trifluoride, nanoparticulate tantalum(V) oxide or barium sulfate. The ytterbium trifluoride preferably has a particle size of from 200 to 800 nm.

Particulate fillers preferably have a particle size of from 0.01 to 15 µm. Nanoparticulate fillers preferably have a particle size of from 10 to 100 nm and microfine fillers preferably have a particle size of from 0.2 to 5 µm. Radiopaque fillers, unless they are nanoparticulate fillers, preferably have a particle size of from 0.2 to 5 µm.

Unless otherwise indicated, all particle sizes are weight-average particle sizes (D50 values), wherein the particle size determination in the range of from 0.1 µm to 1000 µm is preferably effected by means of static light scattering, for example using an LA-960 Static Laser Scattering Particle Size Distribution Analyzer (Horiba, Japan). Here, a laser diode with a wavelength of 655 nm and an LED with a wavelength of 405 nm are used as light sources. The use of two light sources with different wavelengths makes it possible to measure the entire particle size distribution of a specimen in only one measurement pass, wherein the measurement is carried out as a wet measurement. For this purpose, a 0.1 to 0.5% aqueous dispersion of the filler is produced and the scattered light thereof is measured in a flow cell. The scattered light analysis for calculating particle size and particle size distribution is effected in accordance with the Mie theory according to DIN/ISO 13320. The measurement of the particle size in the range of from 5 nm to 0.1 μm is preferably effected by dynamic light scattering (DLS) from aqueous particle dispersions, preferably using an He—Ne laser with a wavelength of 633 nm, at a scattering angle of 90°, and at 25° C., e.g. using a Malvern Zetasizer Nano ZS (Malvern Instruments, Malvern UK).

Particle sizes smaller than 0.1 μm can also be determined by means of SEM or TEM micrographs. The transmission electron microscopy (TEM) is preferably carried out using a Philips CM30 TEM at an accelerating voltage of 300 kV. For the specimen preparation, drops of the particle dispersion are applied to a 50 Å thick copper grid (mesh width 300 mesh), which is coated with carbon, and then the solvent is evaporated. The particles are counted and the arithmetic mean is calculated.

To improve the bond between the filler particles and the crosslinked polymerization matrix, the fillers are preferably surface-modified. $SiO_2$-based fillers are preferably surface-modified with methacrylate-functionalized silanes, particularly preferably with 3-methacryloyloxypropyltrimethoxysilane. For the surface modification of non-silicate fillers, e.g. of $ZrO_2$ or $TiO_2$, functionalized acidic phosphates, such as e.g. 10-methacryloyloxydecyl dihydrogen phosphate, can also be used.

Moreover, the compositions according to the invention can if necessary contain further additives and solvents. The additives are preferably selected from stabilizers, chain transfer reagents, UV absorbers, dyes or pigments and lubricants. Preferred solvents are water, ethanol, acetone, ethyl acetate and mixtures thereof.

The initiators according to formula (I) are characterized by a high photopolymerization reactivity, i.e. the irradiation of small quantities of the compounds of formula (I) is already sufficient to initiate the radical polymerization and thus to cure the compositions. They can therefore be used in low concentrations. The compositions according to the invention contain, relative to the total mass of the composition, preferably 0.001 to 3 wt.-%, particularly preferably 0.001 to 1 wt.-% and quite particularly preferably 0.005 to 0.5 wt.-% of at least one compound of formula (I).

The compounds according to the invention of general formula (I) are particularly suitable as photoinitiators for the production of polymers, composites, cements, coating materials, primers or adhesives. They are particularly suitable for applications in the medical field, above all for the production of dental materials, such as filling composites, fixing cements, adhesives, denture materials, veneering materials, materials for the production of crowns, bridges, inlays, onlays or of coatings.

Further medical fields of use for the compositions according to the invention are found in the field of surgery, e.g. as materials for tissue regeneration or as materials for the production of hearing aids, and in ophthalmology, e.g. for the production of intraocular lenses or contact lenses. By materials for tissue regeneration, e.g. of bone, is meant polymer networks which form the skeletal structure for the incorporation e.g. of the bone material, for example of hydroxyapatite. Such polymer networks can advantageously be produced using the compounds according to the invention of formula (I) as photoinitiators. Because of their high activity these compounds can be used in very low concentrations, which is advantageous with regard to the biological compatibility of the materials.

The possible uses of the compounds according to the invention of formula (I) and of the compositions according to the invention are not limited to the medical field. In the case of technical applications the compounds according to general formula (I) can be used as photoinitiators in stereolithography or in 3D printing, for example in the production of shaped bodies, prototypes or green bodies, for the production of coating materials or in microelectronics, e.g. in photoresist technology.

The compositions according to the invention preferably contain the following constituents:

(a) 0.001 to 3 wt.-%, preferably 0.001 to 1.0 wt.-% and particularly preferably 0.005 to 0.5 wt.-% of at least one compound of general formula (I),
(b) 1 to 99.9 wt.-%, preferably 5 to 95 wt.-% and particularly preferably 10 to 90 wt.-% of at least one radically polymerizable monomer,
(c) 0 to 85 wt.-%, preferably 5 to 80 wt.-% and particularly preferably 10 to 75 wt.-% of at least one filler and
(d) 0 to 70 wt.-%, preferably 0.1 to 60 wt.-% and particularly preferably 0.1 to 50 wt.-% of one or more additives.

All percentages specified herein relate to the total mass of the composition, unless otherwise indicated.

Compositions for use as cements and in particular as dental cements preferably contain:

(a) 0.001 to 3 wt.-%, preferably 0.001 to 1.0 wt.-% and particularly preferably 0.005 to 0.5 wt.-% of at least one compound of general formula (I),
(b) 5 to 70 wt.-%, preferably 10 to 60 wt.-% and particularly preferably 20 to 55 wt.-% of at least one radically polymerizable monomer,
(c) 20 to 80 wt.-%, preferably 20 to 70 wt.-% and particularly preferably 40 to 60 wt.-% of at least one filler and
(d) 0.1 to 10 wt.-%, preferably 1.0 to 10 wt.-% and particularly preferably 1.00 to 5 wt.-% of one or more additives.

Compositions for use as composites and in particular as dental filling composites preferably contain:

(a) 0.001 to 3 wt.-%, preferably 0.001 to 1.0 wt.-% and particularly preferably 0.005 to 0.5 wt.-% of at least one compound of general formula (I),
(b) 5 to 70 wt.-%, preferably 10 to 50 wt.-% and particularly preferably 20 to 40 wt.-% of at least one radically polymerizable monomer,
(c) 30 to 85 wt.-%, preferably 40 to 80 wt.-% and particularly preferably 45 to 77 wt.-% of at least one filler and
(d) 0.1 to 10 wt.-%, preferably 0.5 to 5 wt.-% and particularly preferably 0.5 to 3 wt.-% of one or more additives.

Compositions for use as coating materials and in particular as dental coating materials preferably contain:

(a) 0.001 to 5 wt.-%, preferably 0.001 to 3.0 wt.-% and particularly preferably 0.05 to 3.0 wt.-% of at least one compound of general formula (I),
(b) 10 to 99.9 wt.-%, preferably 15 to 99.9 wt.-% and particularly preferably 30 to 99.9 wt.-% of at least one radically polymerizable monomer,
(c) 0 to 70 wt.-%, preferably 0 to 60 wt.-% and particularly preferably 0 to 20 wt.-% of at least one nanoparticulate filler and
(d) 0.1 to 10 wt.-%, preferably 0.1 to 5 wt.-% and particularly preferably 0.1 to 3 wt.-% of one or more additives,
(e) 0 to 70 wt.-%, preferably 0 to 60 wt.-% and particularly preferably 0 to 50 wt.-% solvent.

Compositions for use as adhesives and in particular as dental adhesives preferably contain:
(a) 0.001 to 5 wt.-%, preferably 0.001 to 3.0 wt.-% and particularly preferably 0.05 to 1.0 wt.-% of at least one compound of general formula (I),
(b1) 1 to 95 wt.-%, preferably 5 to 80 wt.-% and particularly preferably 20 to 80 wt.-% of at least one radically polymerizable monomer,
(b2) 1 to 20 wt.-%, preferably 1.0 to 15 wt.-% and particularly preferably 2 to 15 wt.-% of at least one radically polymerizable adhesive monomer,
(c) 0 to 40 wt.-%, preferably 0 to 30 wt.-% and particularly preferably 1 to 10 wt.-% of at least one nanoparticulate filler and
(d) 0.1 to 10 wt.-%, preferably 0.1 to 5 wt.-% and particularly preferably 0.3 to 5 wt.-% of one or more additives,
(e) 0 to 70 wt.-%, preferably 5 to 60 wt.-% and particularly preferably 10 to 55 wt.-% solvent.

Compositions for use as materials and in particular as dental materials for stereolithography or 3D printing preferably contain:
(a) 0.001 to 3 wt.-%, preferably 0.001 to 1.0 wt.-% and particularly preferably 0.005 to 1.0 wt.-% of at least one compound of general formula (I),
(b) 1 to 99.9 wt.-%, preferably 20 to 98 wt.-% and particularly preferably 30 to 95 wt.-% of at least one radically polymerizable monomer or resin,
(c) 0 to 85 wt.-%, preferably 1 to 70 wt.-% and particularly preferably 3 to 60 wt.-% of at least one filler and
(d) 0.1 to 70 wt.-%, preferably 0.5 to 60 wt.-% and particularly preferably 1.0 to 50 wt.-% of one or more additives.

Compositions according to the invention for dental purposes are particularly suitable for intraoral application by the dentist for the restoration of damaged teeth, i.e. for therapeutic use, e.g. as dental cements, filling composites and veneering materials. However, they can also be used non-therapeutically (extraorally), for example in the production or repair of dental restorations, such as prostheses, artificial teeth, inlays, onlays, crowns and bridges.

Another subject of the invention is the use of a compound according to formula (I) for the production of a radically polymerizable material, preferably a medical-technical and in particular a dental material.

The invention is explained in more detail in the following with reference to examples.

Example 1

Synthesis of 1,2-bis(trismesitoylqermyl)terephthalate 1

1st Stage: Synthesis of tris(mesitoyl) Germanium Enolate TMGe (Method A)

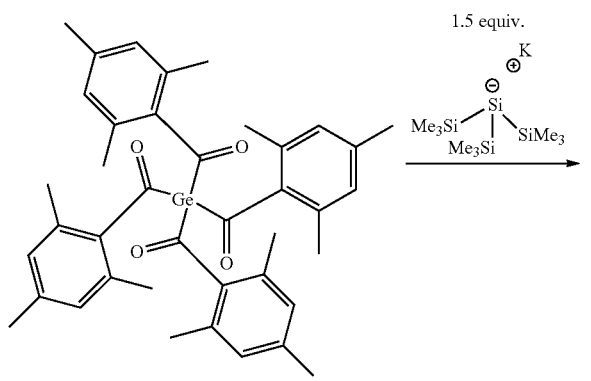
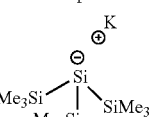

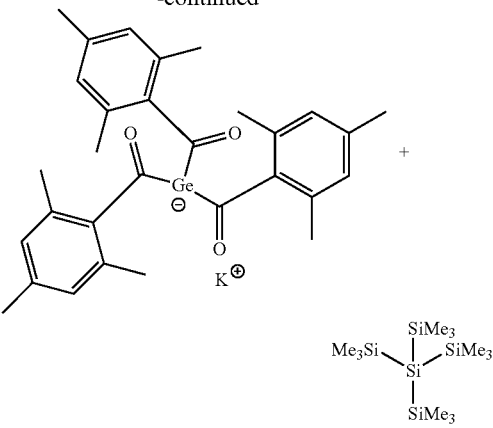
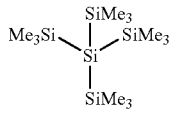

25 mL dimethoxyethane (DME) was added into a flask which contained 2.18 g (6.79 mmol; 1.5 equiv.) tetrakis(trimethylsilyl)silane (Me₃Si)₄Si and 0.76 g potassium tert-t.butylate KOtBu (6.79 mmol; 1.5 equiv.). The reaction mixture for forming the potassium silanide was then stirred for 1 h. In a 2nd flask 3.00 g (4.53 mmol; 1.0 equiv.) tetrakis(mesitoyl)germane was dissolved in 30 mL DME. The potassium silanide solution was added to this slowly by means of a syringe and the reaction solution was stirred for 2 h. The reaction was monitored by means of NMR spectroscopy. The thus obtained tris(mesitoyl) germanium enolate solution can be stored over weeks at −30° C. for further reactions.

1st Stage: Synthesis of tris(mesitoyl) Germanium Enolate TMGe (Method B)

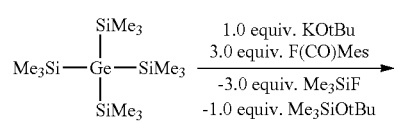

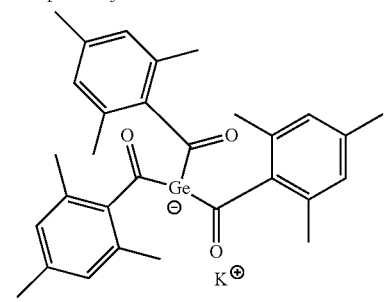

35 mL DME was added into a flask which contained 3.00 g (8.21 mmol) tetrakis(trimethylsilyl)germane (Me₃Si)₄Ge and 1.01 g KOtBu (9.03 mmol; 1.1 equiv.). The reaction mixture was then stirred for 1 h. Then, 1.36 g (8.21 mmol; 1.0 equiv.) mesitoyl fluoride was added and the mixture was stirred for a further 10 minutes. The addition was repeated twice with the same quantity of mesitoyl fluoride (total 2.73 g, 2.0 equiv.) and then the mixture was stirred for another 2 h. The thus obtained tris(mesitoyl) germanium enolate solution can be stored over weeks at −30° C. for further reactions.

Yield:

Method A: 2.8 g (96%). (The germanium enolate TMGe contains a molecule of DME)

Method B: 2.9 g (99%).

$^1$H-NMR: $\delta_H$ (400 MHz, THF-D$_8$): 6.39 (s, 6H, aryl-H), 3.43 (s, 3.2H, CH$_2$), 3.27 (s, 4.5H, CH$_3$), 2.15 (s, 9H, pCH$_3$), 2.04 (s, 18H, oCH$_3$).

$^{13}$C-NMR: $\delta_C$ (100 MHz, THF-D$_8$): 262.77 (GeCOMes), 148.62 (aryl-C1), 135.18 (aryl-C2), 131.63 (aryl-C3) 128.44 (aryl-C4), 72.77 (—CH$_2$—), 58.95 (—CH$_3$), 21.30 (aryl-pCH$_3$), 20.03 (aryl-oCH$_3$).

Melting point: 154-156° C.

UV-VIS: $\lambda$ [nm] ($\varepsilon$ [L mol$^{-1}$ cm$^{-1}$])=427 (3454), 353 (3030).

IR: $\nu$ [cm$^{-1}$]=1604, 1590, 1555, 1535 (m, vC=O).

Elemental analysis: calculated: C: 63.47%, H: 6.74%; found: C: 63.53%, 6.75%.

2nd Stage: Synthesis of
1,2-bis(trismesitoylgermyl)terephthalate 1

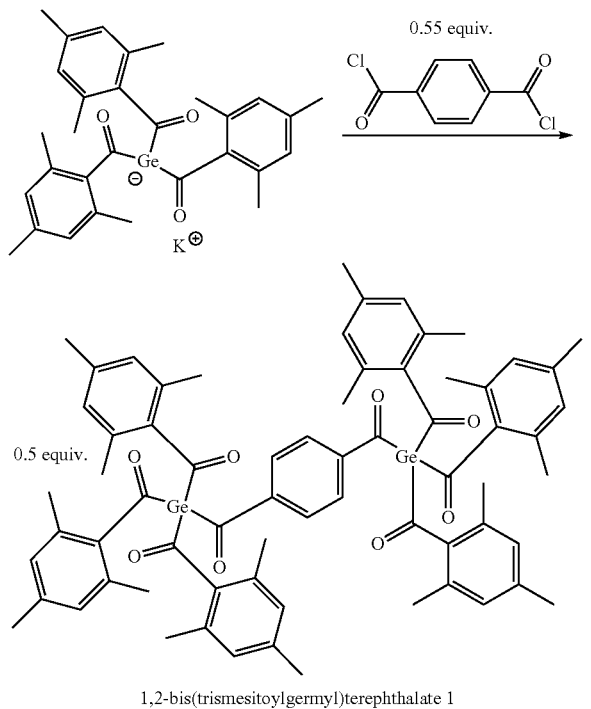

1,2-bis(trismesitoylgermyl)terephthalate 1

0.51 g (2.55 mmol, 0.66 equiv.) terephthaloyl chloride dissolved in 60 mL toluene was added to the solution of tris(mesitoyl) germanium enolate produced according to method A, accompanied by stirring, at −30° C. The reaction solution was heated slowly to room temperature, wherein the reaction monitoring by NMR spectroscopy showed the formation of the 1,2-bis(trismesitoylgermyl)terephthalate 1. After aqueous work-up of the reaction batch with 50 mL saturated NH$_4$Cl solution, the organic phase was separated off and dried over anhydrous Na$_2$SO$_4$. Then, the solution was filtered off and the volatile components were removed in vacuo. The solid residue was recrystallized from acetone and 1.37 g (52% yield) of the 1,2-bis(trismesitoylgermyl)terephthalate 1 was obtained as a yellow crystalline solid.

$^1$H-NMR: $\delta_H$ (400 MHz, CDCl$_3$): 7.22 (s, 4H, aryl-H), 6.56 (s, 12H, aryl-H), 2.15 (s, 18H, pCH$_3$), 2.11 (s, 36H, oCH$_3$).

$^{13}$C-NMR: $\delta_C$ (100 MHz, CDCl$_3$): 231.61, 222.24 (GeC=O), 141.94, 141.33, 140.12, 133.11, 128.87, 128.61 (aryl-C), 21.23 (aryl-pCH$_3$), 19.35 (aryl-oCH$_3$).

Melting point: 245-247° C.

UV-VIS: $\lambda$ [nm] ($\varepsilon$ [L mol$^{-1}$ cm$^{-1}$])=434sh (1645), 377 (5252).

IR: $\nu$ [cm$^{-1}$]=1658, 1643, 1632, 1619, 1607 (m, vC=O).

Elemental analysis: calculated: C: 70.38%, H: 6.08%; found: C: 70.42%, 6.10%.

The 1,2-bis(trismesitoylgermyl)terephthalate 1 produced displayed, with the extinction coefficient of 5252 L mol$^{-1}$ cm$^{-1}$ of the absorption band at 377 nm, a much higher value than the tetrakis(mesitoyl)germane known from the state of the art, with only $\varepsilon$=1984 L mol$^{-1}$ cm$^{-1}$ of the band at 376 nm. The extinction coefficient was also much greater than that of the highly effective commercial photoinitiator bis(4-methoxybenzoyl)diethylgermanium, with $\varepsilon$=724 L mol$^{-1}$ cm$^{-1}$ of the band at 408 nm.

Example 2

Synthesis of
1,2-bis(trismesitoylstannyl)terephthalate 2

1st Stage: Synthesis of tris(mesitoyl) Tin Enolate
TMSn (Method A)

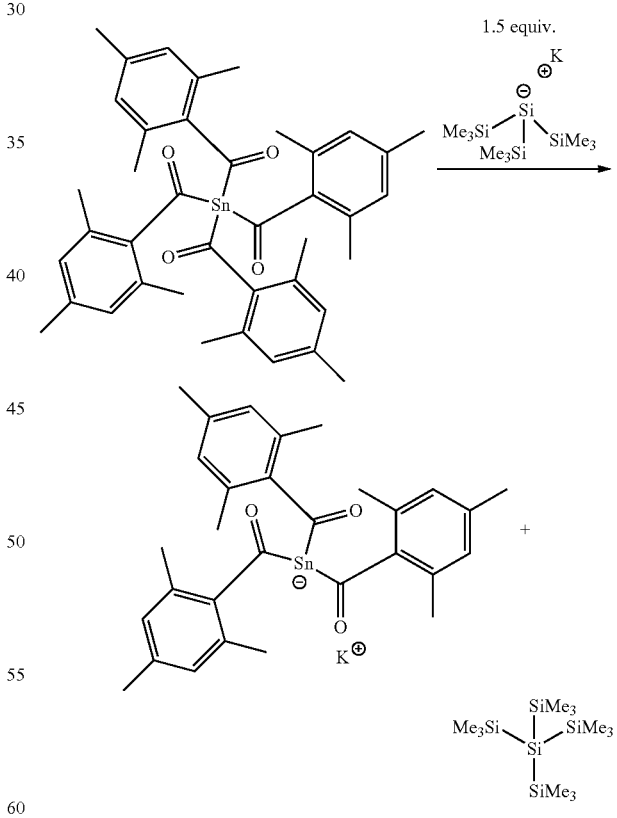

25 mL dimethoxyethane (DME) was added into a flask which contained 2.04 g (6.36 mmol; 1.5 equiv.) tetrakis(trimethylsilyl)silane (Me$_3$Si)$_4$Si and 0.71 g potassium tert.butylate KOtBu (6.36 mmol; 1.5 equiv.). The reaction mixture for forming the potassium silanide was then stirred for 1 h. In a 2nd flask 3.00 g (4.24 mmol; 1.0 equiv.)

tetrakis(mesitoyl)stannane was dissolved in 30 mL DME. The potassium silanide solution was added to this slowly by means of a syringe and the reaction solution was stirred for 2 h. The reaction was monitored by means of NMR spectroscopy. The thus obtained tris(mesitoyl) tin enolate solution could be stored over weeks at −30° C. for further reactions. In order to obtain crystals, 1 equiv. of the crown ether 18-crown-6 was added.

2nd Stage: Synthesis of tris(mesitoyl) Tin Enolate TMSn (Method B)

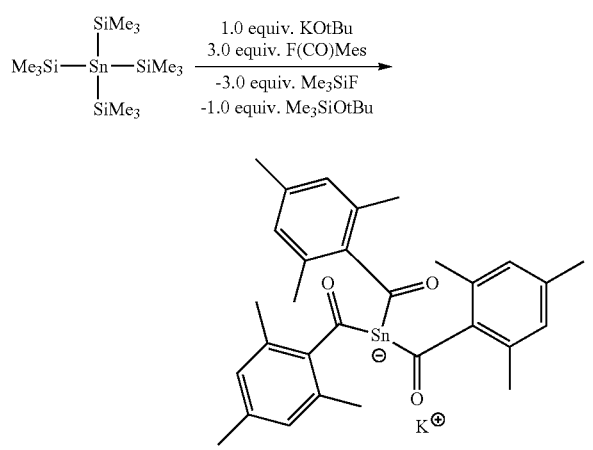

35 mL DME was added into a flask which contains 3.00 g (7.29 mmol) tetrakis(trimethylsilyl)stannane (Me$_3$Si)$_4$Sn and 0.90 g KOtBu (8.02 mmol; 1.1 equiv.). The reaction mixture was then stirred for 1 h. Then, 3.64 g (21.87 mmol; 3.0 equiv.) mesitoyl fluoride was added and the mixture was stirred for a further 30 minutes. The thus obtained tris (mesitoyl) tin enolate solution could be stored over weeks at −30° C. for further reactions. In order to obtain crystals, 1 equiv. of the crown ether 18-crown-6 was added.

Yield:

Method A: 3.1 g (85%) (The tin enolate TMSn contains a molecule of 18-crown-6)

Method B: 5.3 g (84%)

$^1$H-NMR: $\delta_H$ (400 MHz, C$_6$D$_6$): 6.68 (s, 6H, aryl-H), 3.28 (s, 24H (CH$_2$—CH$_2$—O)—), 2.42 (s, 18H, oCH$_3$), 2.17 (s, 9H, pCH$_3$).

$^{13}$C-NMR: $\delta_C$ (100 MHz, C$_6$D$_6$): 286.90 (GeCOMes), 151.17 (aryl-C$_1$), 135.41 (aryl-C$_2$), 130.76 (aryl-C$_3$) 128.91 (aryl-C$_4$), 70.23 (CH$_2$—CH$_2$—O)—, 21.19 (aryl-pCH$_3$), 19.76 (aryl-oCH$_3$).

$^{119}$Sn (C$_6$D$_6$): $\delta$ [ppm]=450.04 (SnCOMes).

Melting point: 165-167° C.

UV-VIS: λ [nm] (ε [L mol$^{-1}$ cm$^{-1}$])=427 (3454), 353 (3030).

IR: v [cm$^{-1}$]=1607, 1581, 1562 (m, vC=O).

Elemental analysis: calculated: C: 58.41%, H: 6.65%; found: C: 58.43%, 6.69%.

2nd Stage: Synthesis of 1,2-bis(trismesitoylstannyl)terephthalate 2

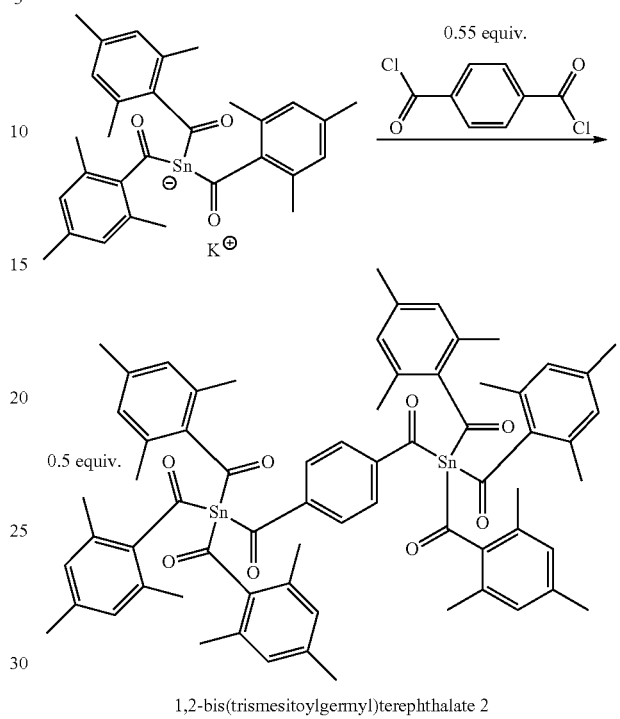

1,2-bis(trismesitoylgermyl)terephthalate 2

0.47 g (2.33 mmol, 0.55 equiv.) terephthaloyl chloride dissolved in 60 mL toluene was added to the solution of tris(mesitoyl) tin enolate produced according to method A, accompanied by stirring, at −30° C. The reaction solution was heated slowly to room temperature, wherein the reaction monitoring by NMR spectroscopy showed the formation of the octaacyl stannane 2. Then, the volatile components were removed from the reaction mixture in vacuo. The solid residue was dissolved in toluene, the insoluble salt portions were filtered off and the filtrate was concentrated to dryness in vacuo. Finally, the solid residue was recrystallized in a mixture of dichloromethane and diethyl ether (2:1) and 1.60 g (60% yield) of the 1,2-bis(trismesitoylstannyl)terephthalate 2 was obtained as a red crystalline solid.

$^1$H-NMR: $\delta_H$ (400 MHz, CDCl$_3$): 7.48 (s, 4H, aryl-H), 6.61 (s, 12H, aryl-H), 2.18 (s, 18H, pCH$_3$), 2.10 (s, 36H, oCH$_3$).

$^{13}$C-NMR: 241.98, 235.36 (SnC=O), 143.53, 143.29, 139.85, 131.69, 128.98, 128.87 (aryl-C), 21.12 (aryl-pCH$_3$), 18.75 (aryl-oCH$_3$).

Melting point: 175-177° C.

UV-VIS: λ [nm] (ε [L mol$^{-1}$ cm$^{-1}$])=470sh (1000), 400 (3200).

IR: v [cm$^{-1}$]=1665, 1625, 1603 (m, vC=O).

Elemental analysis: calculated: C: 65.20%, H: 5.63%; found: C: 65.23%, 5.66%.

The 1,2-bis(trismesitoylstannyl)terephthalate 2 produced displayed, with the extinction coefficient of 4000 L mol$^{-1}$ cm$^{-1}$ of the absorption band at 400 nm, a much higher value than the tetrakis(mesitoyl)stannane known from the state of the art, with ε=1736 L mol$^{-1}$ cm$^{-1}$ of the band at 398 nm, or the highly effective commercial photoinitiator bis(4-methoxybenzoyl)diethylgermanium, with ε=724 L mol$^{-1}$ cm$^{-1}$ of the band at 408 nm.

Example 3

Synthesis of 1,3,5-tris(trismesitoylqermyl)tricarbonylbenzene 3

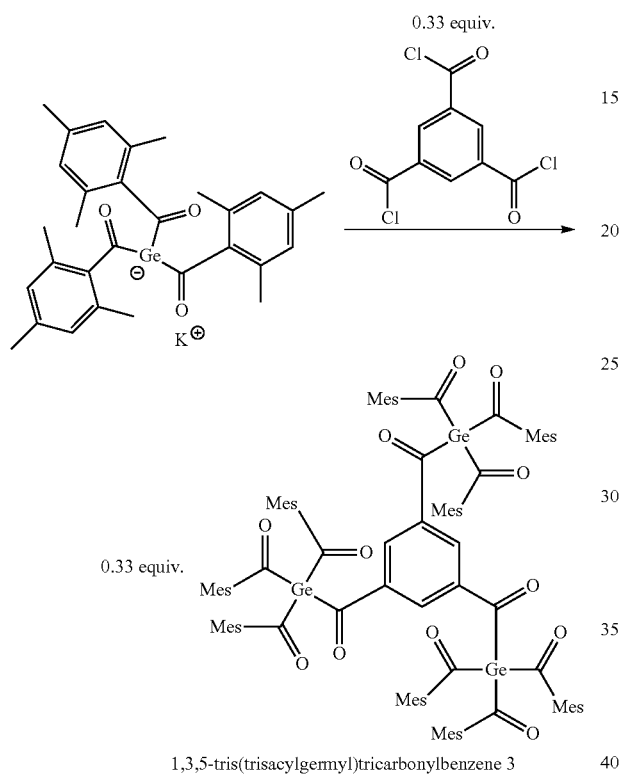

1,3,5-tris(trisacylgermyl)tricarbonylbenzene 3

Method A:

The tris(mesitoyl) germanium enolate was produced analogously to Example 1 according to method A, with 2.18 g (6.79 mmol; 1.5 C) (Me$_3$Si)$_4$Si, 0.76 g KOtBu (6.79 mmol; 1.5 equiv.), 3.00 g (4.53 mmol; 1.0 equiv.) tetrakis(mesitoyl) germane and 25 mL dimethoxyethane (DME). Then, this solution was added to a mixture of 0.40 g (1.50 mmol, 0.33 equiv.) benzene-1,3,5-tricarbonyl trichloride and 60 mL toluene at −30° C. via a syringe. After complete addition, the mixture was heated slowly to room temperature and the reaction was monitored by means of NMR spectroscopy, which indicated the formation of 3. After aqueous work-up of the reaction batch with 50 mL saturated NH$_4$Cl solution, the organic phase was separated off and dried over anhydrous Na$_2$SO$_4$. Then, the solution was filtered off and the volatile components were removed in vacuo. The solid residue was recrystallized from acetone and 1.20 g (52% yield) of the 1,3,5-tris(trismesitoylgermyl)tricarbonylbenzene 3 was obtained as a yellow crystalline analytically pure solid.

Method B:

The tris(mesitoyl) germanium enolate was produced analogously to Example 1 according to method B, with 3.00 g (8.21 mmol) (Me$_3$Si)$_4$Ge, 1.01 g KOtBu (9.03 mmol; 1.1 equiv.), 4.09 g (24.63 mmol; 3.0 equiv.) mesitoyl fluoride and 35 mL DME. Then, this solution was added to a mixture of 0.72 g (2.71 mmol, 0.33 equiv.) benzene-1,3,5-tricarbonyl trichloride and 60 mL toluene at −30° C. via a syringe. After complete addition, the mixture was heated slowly to room temperature and the reaction was monitored by means of NMR spectroscopy, which indicated the formation of 3. After aqueous work-up of the reaction batch with 50 mL saturated NH$_4$Cl solution, the organic phase was separated off and dried over anhydrous Na$_2$SO$_4$. Then, the solution was filtered off and the volatile components were removed in vacuo. The solid residue was recrystallized from acetone and 2.86 g (62% yield) of the tris(trismesitoylgermyl)tricarbonylbenzene 3 was obtained as a yellow crystalline analytically pure solid.

$^1$H-NMR: δ$_H$ (400 MHz, CDCl$_3$): 6.05 (s, 3H, aryl-H), 6.35 (s, 18H, aryl-H), 2.14 (s, 27H, pCH$_3$), 2.12 (s, 54H, oCH$_3$).

$^{13}$C-NMR: 231.05, 219.52 (GeC=O), 141.47, 140.67, 139.78, 133.19, 132.66, 128.94 (aryl-C), 21.26 (aryl-pCH$_3$), 19.41 (aryl-oCH$_3$).

Melting point: 189-192° C.

UV-VIS: λ [nm] (ε [L mol$^{-1}$ cm$^{-1}$])=434sh (1776), 381 (5142).

IR: v [cm$^{-1}$]=1654, 1639, 1606 (m, vC=O)

Elemental analysis: calculated: C: 69.87%, H: 6.04%; found: C: 69.89%, 6.05%.

The tris(trismesitoylgermyl)tricarbonylbenzene 3 produced displayed, with the extinction coefficient of 5142 L mol$^{-1}$ cm$^{-1}$ of the absorption band at 381 nm, a much higher value than the tetrakis(mesitoyl)germane known from the state of the art, with only ε=1984 L mol$^{-1}$ cm$^{-1}$ of the band at 376 nm, or the highly effective commercial photoinitiator bis(4-methoxybenzoyl)diethylgermanium, with ε=724 L mol$^{-1}$ cm$^{-1}$ of the band at 408 nm.

Example 4

Synthesis of 1,4-bis(trismesitoylqermyl)butane 4

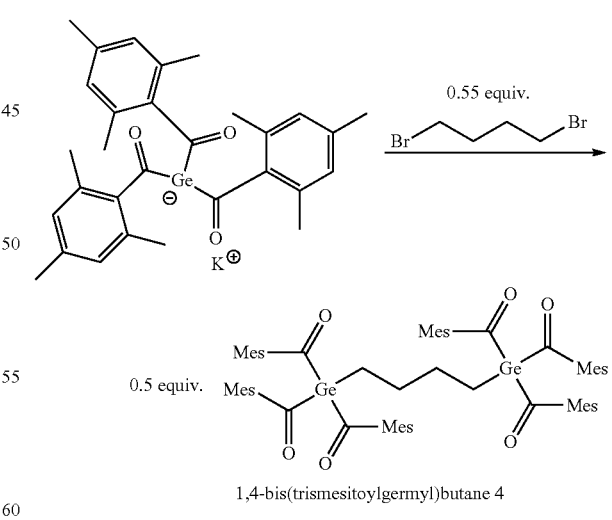

1,4-bis(trismesitoylgermyl)butane 4

Method A:

The tris(mesitoyl) germanium enolate was produced analogously to Example 1 according to method A, with 2.18 g (6.79 mmol; 1.5 C) (Me$_3$Si)$_4$Si, 0.76 g KOtBu (6.79 mmol; 1.5 equiv.), 3.00 g (4.53 mmol; 1.0 equiv.) tetrakis(mesitoyl) germane and 25 mL dimethoxyethane (DME). Then, this solution was added to a mixture of 0.54 g (2.49 mmol, 0.55 equiv.) 1,4-dibromobutane and 60 mL toluene at −30° C. via a syringe. After complete addition, the mixture was heated slowly to room temperature and the reaction was monitored by means of NMR spectroscopy, which indicated the formation of 4. After aqueous work-up of the reaction batch with 50 mL saturated NH$_4$Cl solution, the organic phase was separated off and dried over anhydrous Na$_2$SO$_4$. Then, the solution was filtered off and the volatile components were removed in vacuo. The solid residue was recrystallized from n-pentane and 1.60 g (65% yield) of the 1,4-bis(trismesitoylgermyl)butane 4 was obtained as a yellow crystalline analytically pure solid.

Method B:

The tris(mesitoyl) germanium enolate was produced analogously to Example 1 according to method B, with 3.00 g (8.21 mmol) (Me$_3$Si)$_4$Ge, 1.01 g KOtBu (9.03 mmol; 1.1 equiv.), 4.09 g (24.63 mmol; 3.0 equiv.) mesitoyl fluoride and 35 mL DME. Then, this solution was added to a mixture of 0.98 g (4.51 mmol, 0.55 equiv.) 1,4-dibromobutane and 60 mL toluene at −30° C. via a syringe. After complete addition, the mixture was heated slowly to room temperature and the reaction was monitored by means of NMR spectroscopy, which indicated the formation of 3. After aqueous work-up of the reaction batch with 50 mL saturated NH$_4$Cl solution, the organic phase was separated off and dried over anhydrous Na$_2$SO$_4$. Then, the solution was filtered off and the volatile components were removed in vacuo. The solid residue was recrystallized from acetone and 3.34 g (75% yield) of the 1,4-bis(trismesitoylgermyl)butane 4 was obtained as a yellow crystalline analytically pure solid.

$^1$H-NMR: δ$_H$ (400 MHz, CDCl$_3$): 6.68 (s, 12H, aryl-H), 2.26 (s, 18H, pCH$_3$), 2.04 (s, 36H, oCH$_3$), (bs, 8H, —(CH$_2$)$_4$—).

$^{13}$C-NMR: 237.45 (GeC=O), 142.16, 139.30, 132.49, 128.83, (aryl-C), 27.52, 16.75 (CH$_2$—C), 21.26 (aryl-pCH$_3$), 19.10 (aryl-oCH$_3$).

Melting point: 180-181° C.

UV-VIS: λ [nm] (ε [L mol$^{-1}$ cm$^{-1}$])=400 (1982), 382 (2628).

IR: ν [cm$^{-1}$]=1650, 1632, 1627, 1606 (m, νC=O)

Elemental analysis: calculated: C: 70.88%, H: 6.88%; found: C: 70.89%, 6.87%.

The 1,4-bis(trismesitoylgermyl)butane 4 produced displayed, with the extinction coefficient of 2628 L mol$^{-1}$ cm$^{-1}$ of the absorption band at 382 nm, a much higher value than the tetrakis(mesitoyl)germane known according to the state of the art, with only ε=1984 L mol$^{-1}$ cm$^{-1}$ of the band at 376 nm, or the highly effective commercial photoinitiator bis(4-methoxybenzoyl)diethylgermanium, with ε=724 L mol$^{-1}$ cm$^{-1}$ of the band at 408 nm.

Example 5

Production of Light-Curable Composites Using 1,4-bis(trismesitoylqermyl)butane 4 from Example 4

From a mixture (specified in mass-%) of the dimethacrylates bis-GMA (addition product of methacrylic acid and bisphenol A diglycidyl ether) and bis(methacryloyloxymethyl)tricyclo-[5.2.1.0$^{2,6}$]decane (DCP), the respective photoinitiator and filler (silanized glass filler GM 27884, 0.7 μm, Schott), the light-curing composites C$_1$ and C$_2$ (reference composite) were produced by means of a roll mill ("Exakt" model, Exakt Apparatebau, Norderstedt) (Table 1).

TABLE 1

Composition of the composites C1 and C2

| Component | C1 | C2*) |
|---|---|---|
| Photoinitiator: 1,4-bis(trismesitoylgermyl)butane 4 | 0.05 | — |
| Photoinitiator: bis(4-methoxybenzoyl)diethylgermanium | — | 0.05 |
| DCP | 17.47 | 17.47 |
| Bis-GMA | 17.48 | 17.48 |
| Glass filler GM 27884, sil. | 65.00 | 65.00 |

*)Comparison example

The determination of the flexural strength (FS) and of the flexural modulus of elasticity (FM) of the materials was effected in accordance with ISO standard ISO 4049 (Dentistry—Polymer-based filling, restorative and luting materials). For this, test pieces were prepared, which were irradiated twice for 40 s in an irradiation chamber (from Hönle, Gräfelfing) with light of a wavelength of 410 nm and of 460 nm simultaneously and thus cured. Flexural strength (FS) and flexural modulus of elasticity (FM) were measured after 24 h of storage in water with a temperature of 37° C. (WS) (Table 2).

TABLE 2

Flexural strength (FS, MPa) and flexural modulus of elasticity (FM, GPa) of the polymerized composites C1 and C2

|  | C1 | C2*) |
|---|---|---|
| FS, WS | 104.6 ± 13.2 | 122.0 ± 13.1 |
| FM, WS | 5.30 ± 0.39 | 6.72 ± 0.84 |

*)Comparison example

The results in Table 2 demonstrate the very good polymerization-initiating action of the 1,4-bis(trismesitoylgermyl) butane 4 according to the invention, even compared with the commercial photoinitiator bis(4-methoxybenzoyl)diethylgermanium, which is much more difficult to obtain and accordingly very expensive.

The invention claimed is:

1. A compound according to general formula (I)

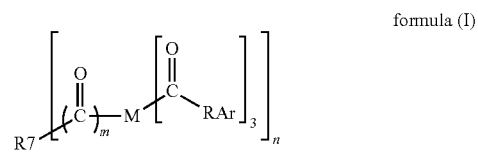

formula (I)

in which the variables have the following meanings:
M Ge or Sn,
RAr

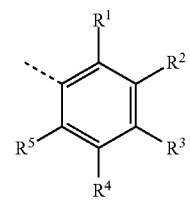

$R^1$, $R^2$, $R^3$, $R^4$, $R^5$ independently of one another in each case —H, —F, —Cl, —OR$^6$, —SR$^6$, —N(R$^6$)$_2$, —CF$_3$, —CN, —NO$_2$, —COOR$^6$, —CONHR$^6$, a branched, cyclic or linear $C_{1-20}$ alkyl, $C_{2-20}$ alkenyl, $C_{1-20}$ alkyloxy or a $C_{2-20}$ alkenoxy radical, which can be interrupted one or more times by O, S or —$NR^6$— and which can be substituted by one or more polymerizable groups and/or radicals $R^6$, $R^6$ in each case independently of one another H, a branched, cyclic or linear $C_{1-20}$ alkyl or $C_{2-20}$ alkenyl radical, $R^7$ an n-valent aromatic radical or a branched, cyclic or linear $C_{2-20}$ alkylene radical, which can be interrupted one or more times by O, S or —$NR^6$— and which can be substituted by one or more polymerizable groups, =O and/or radicals $R^6$, n 2 or 3,
m 0 or 1.

2. The compound according to claim 1, wherein the variables of formula (I) have the following meanings:
M Ge or Sn,
RAr

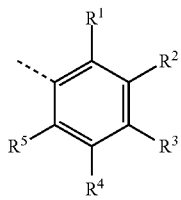

$R^1$, $R^2$, $R^3$, $R^4$, $R^5$ independently of one another in each case —H, —F, —Cl, —$OR^6$, —$CF_3$, —CN, —$COOR^6$, —$CONHR^6$, a linear $C_{1-20}$ alkyl, $C_{2-20}$ alkenyl, $C_{1-20}$ alkyloxy or a $C_{2-20}$ alkenoxy radical, which can be interrupted one or more times by O or S and which can be substituted by one or more polymerizable groups and/or radicals $R^6$;

$R^6$ H, an aromatic radical or a linear $C_{1-10}$ alkyl radical, $C_{2-10}$ alkenyl radical, $R^7$ a branched or linear n-valent $C_{2-10}$ alkylene radical, which can be interrupted one or more times by O or S and which can be substituted by one or more polymerizable groups, =O and/or radicals $R^6$, n 2,
m 0 or 1.

3. The compound according to claim 1, wherein the variables of formula (I) have the following meanings:
M Ge or Sn,
RAr

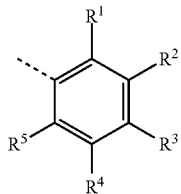

$R^1$, $R^2$, $R^3$, $R^4$, $R^5$ independently of one another in each case —H or a $C_{1-3}$ alkyl radical,
$R^7$ an n-valent benzene radical or an n-valent, linear $C_{2-8}$ alkyl radical,
n 2,
m 0 or 1.

4. The compound according to claim 1, wherein the variables of formula (I) have the following meanings:
M Ge or Sn,
RAr

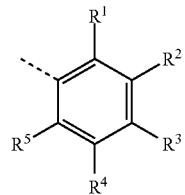

$R^1$, $R^2$, $R^3$, $R^4$, $R^5$ independently of one another in each case —H or methyl,
$R^7$ an n-valent benzene radical or an n-valent, linear $C_{2-6}$ alkyl radical,
n 2,
m 0 or 1.

5. The compound according to claim 1, wherein the variables of formula (I) have the following meanings:
M Ge or Sn
RAr

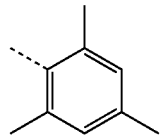

$R^7$

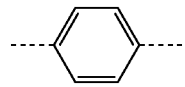

n 2
m 1.

6. The compound according to claim 1, wherein the variables of formula (I) have the following meanings:
M Ge
RAr

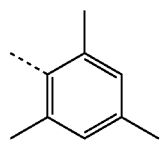

$R^7$

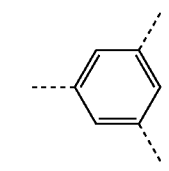

n 3
m 1.

7. The compound according to claim 1, wherein the variables of formula (I) have the following meanings:

M Ge

RAr

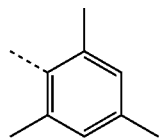

$R^7$ $C_2$-$C_8$ alkylene, particularly preferably —$C_4H_8$— n 2 m 0.

8. A composition which comprises at least one compound according to general formula (I)

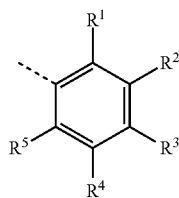
formula (I)

in which the variables have the following meanings:

M Ge or Sn,

RAr

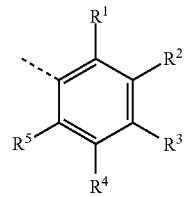

$R^1$, $R^2$, $R^3$, $R^4$, $R^5$ independently of one another in each case —H, —F, —Cl, —$OR^6$, —$SR^6$, —$N(R^6)_2$, —$CF_3$, —CN, —$NO_2$, —$COOR^6$, —$CONHR^6$, a branched, cyclic or linear $C_{1-20}$ alkyl, $C_{2-20}$ alkenyl, $C_{1-20}$ alkyloxy or a $C_{2-20}$ alkenoxy radical, which can be interrupted one or more times by O, S or —$NR^6$— and which can be substituted by one or more polymerizable groups and/or radicals $R^6$, $R^6$ in each case independently of one another H, a branched, cyclic or linear $C_{1-20}$ alkyl or $C_{2-20}$ alkenyl radical, $R^7$ an n-valent aromatic radical or a branched, cyclic or linear $C_{2-20}$ alkylene radical, which can be interrupted one or more times by O, S or —$NR^6$— and which can be substituted by one or more polymerizable groups, =O and/or radicals $R^6$, n 2 or 3, m 0 or 1; and at least one polymerizable monomer.

9. The composition which comprises at least one compound according to general formula (I)

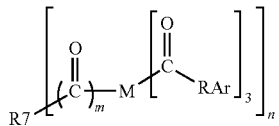
formula (I)

in which the variables have the following meanings:

M Ge or Sn,

RAr

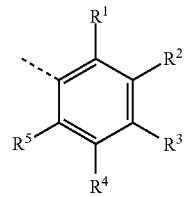

$R^1$, $R^2$, $R^3$, $R^4$, $R^5$ independently of one another in each case —H, —F, —Cl, —$OR^6$, —$SR^6$, —$N(R^6)_2$, —$CF_3$, —CN, —$NO_2$, —$COOR^6$, —$CONHR^6$, a branched, cyclic or linear $C_{1-20}$ alkyl, $C_{2-20}$ alkenyl, $C_{1-20}$ alkyloxy or a $C_{2-20}$ alkenoxy radical, which can be interrupted one or more times by O, S or —$NR^6$— and which can be substituted by one or more polymerizable groups and/or radicals $R^6$, $R^6$ in each case independently of one another H, a branched, cyclic or linear $C_{1-20}$ alkyl or $C_{2-20}$ alkenyl radical, $R^7$ an n-valent aromatic radical or a branched, cyclic or linear $C_{2-20}$ alkylene radical, which can be interrupted one or more times by O, S or —$NR^6$— and which can be substituted by one or more polymerizable groups, =O and/or radicals $R^6$, n 2 or 3, m 0 or 1; and at least one radically polymerizable monomer.

10. The composition according to claim 9, which comprises 0.001 to 3 wt.-% of the at least one compound according to general formula (I), relative to the total mass of the composition.

11. The composition according to claim 10, which comprises 0.001 to 1 wt.-% of the at least one compound according to general formula (I), relative to the total mass of the composition.

12. The composition according to claim 10, which comprises 0.005 to 0.5 wt.-% of the at least one compound according to general formula (I), relative to the total mass of the composition.

13. The composition according to claim 9, which comprises at least one mono- or multifunctional (meth)acrylate or a mixture thereof as the at least one radically polymerizable monomer.

14. The composition according to claim 9, which comprises (a) 0.001 to 3 wt.-% of at least one compound of general formula (I), (b) 1 to 99.9 wt.-% of at least one radically polymerizable monomer, (c) 0 to 85 wt.-% of at least one filler and (d) 0 to 70 wt.-% of one or more additives, in each case relative to the total mass of the composition.

15. The composition according to claim 14, which comprises
- (a) 0.001 to 1.0 wt.-% of at least one compound of general formula (I),
- (b) 5 to 95 wt.-% of at least one radically polymerizable monomer,
- (c) 5 to 80 wt.-% of at least one filler and
- (d) 0.1 to 60 wt.-% of one or more additives, in each case relative to the total mass of the composition.

16. The composition according to claim 14, which comprises
- (a) 0.005 to 0.5 wt.-% of at least one compound of general formula (I),
- (b) 10 to 90 wt.-% of at least one radically polymerizable monomer,
- (c) 10 to 75 wt.-% of at least one filler and
- (d) 0.1 to 50 wt.-% of one or more additives, in each case relative to the total mass of the composition.

17. The composition according to claim 8 for therapeutic use as a dental material, preferably as a dental cement, filling composite or veneering material.

18. The compound according to claim 1 for use as a photoinitiator.

\* \* \* \* \*